United States Patent [19]

Husu et al.

[11] Patent Number: 5,079,237
[45] Date of Patent: Jan. 7, 1992

[54] INCLUSION COMPLEX OF NICARDIPINE OR ITS HYDROCHLORIDE WITH BETA-CYCLODEXTRIN AND A SUSTAINED RELEASE PHARMACEUTICAL PREPARATION CONTAINING THE SAME

[75] Inventors: Breda Husu; Jenny Milovac, both of Ljubljana; Zdravok Kopitar, Mengeš; Branko Huč, Ljubljana; Janko Žmitek, Ljubljana; Peter Bukovec, Ljubljana; Mirjan Žorž, Grosuplje; Boris Rusjakovski, Ljubljana; Polona Cvelbar, Velike Lašče; Zdenka Jerala-Štrukelj, Mavčiče; Bojan Kofler, Škofja Loka, all of Yugoslavia

[73] Assignee: Lek, Yugoslavia

[21] Appl. No.: 298,151

[22] Filed: Jan. 18, 1989

[30] Foreign Application Priority Data

Jan. 18, 1988 [YU] Yugoslavia ............................ P 82/88

[51] Int. Cl.[5] .................. A61K 31/455; C07D 211/90
[52] U.S. Cl. ....................................... 514/58; 536/103; 514/929; 514/964; 514/778; 514/781; 514/356; 424/488; 424/486; 424/457; 424/468
[58] Field of Search .................. 536/103; 514/58, 929, 514/964, 778, 781; 424/80, 488, 486, 457, 468

[56] References Cited

U.S. PATENT DOCUMENTS

| | | | |
|---|---|---|---|
| 4,383,992 | 5/1983 | Lipari | 424/238 |
| 4,555,504 | 11/1985 | Jones | 536/103 |
| 4,727,064 | 2/1988 | Pitha | 536/103 |
| 4,826,963 | 5/1989 | Stadler et al. | 536/103 |
| 4,869,904 | 9/1989 | Uekama et al. | 424/456 |
| 4,952,565 | 8/1990 | Zmitek et al. | 514/777 |

FOREIGN PATENT DOCUMENTS

| | | |
|---|---|---|
| 251459 | 1/1988 | European Pat. Off. |
| 63-218663 | 9/1988 | Japan |
| 2016499 | 9/1979 | United Kingdom |

OTHER PUBLICATIONS

Fairchild, Editor, Suspected Carcinogens, A Sourcebook of the Toxic Effects of Chemical Substances, Castle House Publications, Ltd, 1978, I.S.B. No.-7194-00-00-7-Printed in Great Britain by Billing & Sons Limited, Guildford, p. 191, item TZ29750.

E. Fenyvesi et al., "Properties of Cyclodextrin Polymer as a Tablething Aid", Chem. Pharm. Bull. 32(2), 665-669 (1984).

M. Kurozumi et al, "Inclusion Compounds of Non-Steroidal Antiinflammatory and Other Slightly Water Soluble Drugs with α- and β-Cyclohdextrins in Powdered Form", Chem. Pharm. Bull. 23(12), 3062-3068 (1975).

Stadler-Szoke et al., "A Forecast for Application of Cyclodextrins in the Pharma-Industry", I. Int. Symp. on Cyclodextrins, Budapest, 30 Sep. -2 Oct. 1981, 5.2, p. 377.

(List continued on next page.)

*Primary Examiner*—Ronald W. Griffin
*Attorney, Agent, or Firm*—Pollock, Vande Sande & Priddy

[57] ABSTRACT

There is described a new inclusion complex of nicardipine or its hydrochloride with beta-cyclohdextrin, which is prepared by admixing nicardipine or its hydrochloride with beta-cyclodextrin in a molar ratio of the compounds 1:0.9-1.1 under stirring at a temperature from about room temperature to the boiling temperature of the reaction mixture in an aqueous or ethanolic medium, cooling the reaction mixture to 0° to 5° C. and isolating the desired complex.

The inclusion complex of nicardipine or its hydrochloride posesses cerebrovascular-vasodilatory and coronary-vasodilatory properties, which are equally well expressed as those of nicardipine or its hydrochloride themselves, yet owing to the better solubility of the complex at a higher pH range, such as it exists e.g. in the intestinal tract, the manufacture of sustained release pharmaceutical forms is made possible, whereby a greater extent of dissolution of the active substance is provided also in the intestinal juice.

9 Claims, 6 Drawing Sheets

OTHER PUBLICATIONS

Thuillez et al., "Nicardipine: Pharmacokinetics and Effects on Carotid and Brachial Blood Flows in Normal Volunteers", Br. J. Clin. Pharmac. (1984), 18, pp. 837–847.

Pitha et al., "Hydroxypropyl-β-Cyclodextrin: Preparation and Characterization; Effects on Solubility of Drugs", Int. J. of Pharm. 29 (1986), pp. 73–82.

Budavari, Editor, The Merck Index, 11th ed. 1989, p. 1247, item 7869, published by Merck & Co., Inc., Rahway, N.J., U.S.A.

Uekama et al, "Ethylated β-Cyclodextrins as Hydrophobic Drug Carriers: Sustained Release of Diltiazem in the Rat", Journal of Pharmaceutical Sciences, vol. 76, No. 8, Aug. 1987, pp. 660–661.

Hirayama et al, "Utilization of Diethyl-β-Cyclodextrin as a Sustained-Release Carrier for Isosobide Dinitrate", Journal of Pharmaceutical Sciences, vol. 77, No. 3, Mar. 1988, pp. 233–236.

Horiuchi et al., "Slow-Release Characteristics of Diltiazem from Ethylated β-Cyclodextrin Complexes", Journal of Pharmaceutical Sciences, vol. 79, No. 2, 1990, pp. 128–132.

Chemical Abstracts, vol. 101, Abstract 101:230946w, 1984.

Chemical Abstracts, vol. 110, abstract 110:101775b, Mar. 20, 1989.

Szejitli et al, "Synthesis and C-NMR Spectroscopy of Methylated Beta-Cyclodextrins", Starch Stärke (1980), vol. 32, No. 5, pp. 165–169.

The Merck Index, 11th edition (1989), pp. 493–494, item 3120.

Szejtli, Cyclodextrin Technology, 1988 published by Kluever Academic Publishers, Boston, Mass., pp. 80–83.

FIG. 1a

FIG.1c

INCLUSION COMPLEX OF NICARDIPINE OR ITS HYDROCHLORIDE WITH BETA-CYCLODEXTRIN AND A SUSTAINED RELEASE PHARMACEUTICAL PREPARATION CONTAINING THE SAME

TECHNICAL FIELD OF THE INVENTION (IPC A 61 K 31/435)

The invention belongs to the field of pharmaceutical industry and relates to a novel inclusion complex of nicardipine or its hydrochloride with β-cyclodextrin and to a sustained release pharmaceutical preparation containing the same.

Nicardipine is in the form of its hydrochloride salt a valuable substance having cerebrovascular-vasodilatory as well as coronary-vasodilatory activity.

By the conversion of nicardipine or its hydrochloride to the inclusion complex with beta-cyclodextrin, its aqueous solubility as well as the rate and extent of its dissolution within the range of greater pH values, such as the one existing e.g. in intestinal tract, is increased.

TECHNICAL PROBLEM

Because of the poor solubility of nicardipine or its hydrochloride in biological fluids having a pH of 5 to 8, there exists a constant need for the conversion of nicardipine or its hydrochloride to a form having improved solubility in the intestinal juice with a pH of 5 to 8. The increased rate and extent of dissolution make possible the preparation of a sustained release pharmaceutical form whenever it is necessary to ensure the dissolution of nicardipine or its hydrochloride also in the intestinal juice.

Prior Art

Nicardipine is the generic name for 2-(N-benzyl-N-methylamino)-ethyl methyl 2,6-dimethyl-4-(m-nitrophenyl)-1,4-dihydropyridine-3,5-dicarboxylate of the formula Nicardipine was disclosed for the first time in DE patent 24 07 115 as a substance having valuable cerebrovascular-vasodilatory and coronary-vasodilatory properties. Nicardipine in the form of its hydrochloride salt is used in the therapy of cerebral insufficiency and as an antihypertensive agent.

Numerous derivatives of 1,4-dihydro-pyridine-3,5-dicarboxylic acid are known from literature sources (Chem. Ber. 20, 1338–1343 (1987) and J. Am. Chem. Soc. 71, 4003–4007 (1949)). The use of these compounds for therapeutical purposes was described for the first time in U.S. Pat. No. 3,644,627 for dimethyl 4-(o-nitrophenyl)-2,6-dimethyl-1,4-dihydropyridine-3,5-dicarboxylate, which is known under the generic name nifedipine and has coronary-vasodilatory properties.

It is known that nifedipine has a very poor water solubility, which makes the preparation of suitable pharmaceutical preparations difficult. For numerous other 1,4-dihydropyridine-3,5-dicarboxylic acid derivatives described thereafter, their poor water solubility is characteristic as well.

It is known that 1,4-dihydropyridine-3,5-dicarboxylic acid derivatives, which were described in DE patent 24 07 115, where nicardipine was described for the first time, can form water soluble salts with mineral acids, wherein they differ from related substances described in earlier literature. Nicardipine and related compounds described in DE patent 24 07 115 as having low toxicity as well as salts of these compounds are known to be suitable for liquid pharmaceutical preparations (especially injections) owing to their water solubility. Yet the water solubility of nicardipine and its hydrochloride as well as that of their sustained release preparations is still unsatisfactory. Furthermore, it is known that the solubility of nicardipine hydrochloride is good at low pH values, whereas it is very poor at higher pH values. Therefore nicardipine hydrochloride is likely to be absorbed only in the stomach and in the upper part of the intestinal tract.

There are well-known difficulties encountered when preparing pharmaceutical formulations from therapeutically active substances having poor water solubility as well as other problems, e.g. dissolution difficulties, i.e. a poor rate of release and hence a poor or variable bioavailability.

To overcome these difficulties, with substances having a very poor water solubility there has been used complexing with cyclodextrins although the complexes are not always efficient.

It is known that cyclodextrins form inclusion complexes with other molecules of suitable size and polarity (J. Pharm. Sci. 64, 1585, 1975). Cyclodextrins are cyclic compounds, consisting of 6, 7 or 8 glucopyranose units linked together by alpha-1,4-glycosidic bonds. They are characterized by a cylindric structure and a special arrangement of hydroxyl groups, whereby the outer surface of the ring formed by cyclodextrin is hydrophilic, ensuring water solubility, whereas the inner surface is lipophilic, which permits other molecules, known as "guest molecules" or parts thereof, which are less polar than water (hydrophobic molecules) and are of suitable dimensions, to penetrate the lipophilic cavity of the inner part of the cylindric cyclodextrin molecule, forming thereby the inclusion complex.

DESCRIPTION OF THE SOLUTION OF THE TECHNICAL PROBLEM WITH Examples

The object of the present invention is to convert nicardipine or its hydrochloride to a form having a substantially increased rate and extent of dissolution within the range of greater pH values, such as it exists e.g. in the intestinal tract.

Such a property makes possible the preparation and the use of a sustained release pharmaceutical form, whenever it is necessary to ensure the dissolution of nicardipine hydrochloride also in the intestinal juice.

This object is achieved by bonding nicardipine or its hydrochloride into the structure of the cyclodextrin molecule, whereby a new inclusion complex with an increased water solubility is formed as a yellowish microcrystallinic product.

From among different cyclodextrins there can be used alpha-cyclodextrin, beta-cyclodextrin and gammacyclodextrin, preferably beta-cyclodextrin. The complex may be prepared by methods known for the preparation of inclusion complexes with cyclodextrins.

The process for preparing the inclusion complex of nicardipine or its hydrochloride with beta-cyclodextrin is performed by reacting nicardipine or its hydrochloride with beta-cyclodextrin in a molar ratio of the components of about 1:1 under stirring at a temperature from room temperature to the boiling point of the reaction mixture in an aqueous or ethanolic medium, cooling the reaction mixture and isolating the desired complex.

The admissible deviation from the 1:1 molar ratio is ±10% at the most, i.e. the molar ratio can be 1:0.9 to 1.1.

The invention also relates to sustained release pharmaceutical preparations, comprising a therapeutically effective amount of the inclusion complex of nicardipine or its hydrochloride with beta-cyclodextrin together with a pharmaceutically acceptable carrier and other common excipients.

Pharmaceutical compositions are preferably formulated in forms suitable for oral application, such as tablets, capsules etc. At formulating it should be taken into consideration that the content of nicardipine or its hydrochloride in the complex is in the range from 14 to 18% or from 25 to 31%, respectively. The resulting complex is administered orally, the cyclodextrin acting merely as a solubilizing agent and not altering the therapeutic behaviour of the active substance in any way.

Oral sustained release pharmaceutical preparations (tablets, capsules) are prepared by incorporating the inclusion complex of nicardipine hydrochloride with beta-cyclodextrin into a hydrophilic matrix, across which the active substance passes in a controlled way by diffusion and slow erosion of the matrix.

For the preparation of the matrix there are used sodium alginate (type Manucol®, Kelco Company), which is present in pharmaceutical preparations in an amount from 40 to 56% by weight, or high-molecular celluloses, such as methyl cellulose, hydroxypropyl cellulose or hydroxypropyl methylcellulose of various viscosity grades, such as hydroxypropyl methylcellulose having a viscosity of 4000 cp (Methocel® E4M, The Dow Chemical Co.), which is present in pharmaceutical preparations in an amount from 10 to 30% by weight.

The tablets may also contain other ingredients, which are used for the manufacture of tablets or capsules, such as from 1 to 5% of glycerol tripalmitostearate (Precirol Ato 5, Gattefossee Comp.) as a pharmaceutically acceptable inert fatty substance, acting as a sustained release lubricant, or other lubricants, such as magnesium stearate, stearic acid and the like, solubility improving surfactants, such as sodium lauryl sulfate (Texapon® K 12), binders, fillers and the like. Polyvinylpyrrolidone is contained in tablets and capsules in an amount from 5.0 to 6.5% by weight.

Sustained release tablets and capsules are prepared using the inclusion complex of nicardipine hydrochloride with beta-cyclodextrin containing 25% of nicardipine hydrochloride. Thus, the pharmaceutical preparation for oral administration contains a dosage of 60 mg of nicardipine hydrochloride together with other carriers and excipients.

The invention is illustrated in more detail by the following Examples, which are not intended to be a limitation thereof.

EXAMPLE 1

Preparation of the inclusion complex of nicardipine hydrochloride with beta-cyclodextrin Beta-cyclodextrin (3.609 g; 3 mmoles, water content about 6%) was suspended under stirring in distilled water (150 ml). Nicardipine hydrochloride (1.548 g; 3 mmoles) was added and the resulting mixture was stirred at room temperature for two days.

The nearly clear solution was kept in refrigerator (at a temperature of 4° C.) for 2 hours and the separated precipitate was then filtered off. The clear solution was evaporated in vacuo to a dry product, which was then dried at a pressure of 400 mbar and at a temperature of 100 ° C. to constant weight.

Thus, there were obtained 4.593 g (93%) of a yellow microcrystalline product, m.p. 240°–245° C.

The product contained 1.36% of water (determined according to Karl-Fischer) and 31% of pure nicardipine in the complex as shown by HPLC at 350 nm (column: RP-18; 10 /um; 150×4 mm; eluent: $CH_3OH:CH_3CN:0.05M$ sodium acetate 800:200:300; flow rate 2 ml/min).

EXAMPLE 2

Preparation of the inclusion complex of nicardipine (base) with beta-cyclodextrin Nicardipine (1.5 g; 3.13 mmoles; as an oily base) was dissolved in 96% ethanol (60 ml) and the solution was heated to a temperature of 50° C. At the same temperature beta-cyclodextrin (5 g; 4.15 mmoles; water content 6%) in distilled water (120 ml) was added dropwise. The clear solution, which subsequently became cloudy, was stirred for another half an hour at room temperature and then the reaction mixture was cooled in a freezer. After two to three hours a pale yellow product separated, which was filtered off and dried at first at a pressure of 400 mbar and a temperature of 40° C. and then at the same pressure and at a temperature of 80° C.

2 g of the obtained product were suspended in 40 ml of distilled water and the suspension was stirred at room temperature for 12 hours. Then the suspension was cooled to a temperature of 4° C., the undissolved part was filtered off and the clear solution was evaporated in vacuo to a dry powdery product.

Thus, there were obtained 1.9 g (29.2%) of a yellow microcrystalline product, m.p. 250° C. (with decomposition).

HPLC determination of nicardipine (base) content in the complex at 350 nm showed a value of 15.5%.

EXAMPLE 3

Solubility in water

Comparative solubility of nicardipine and its hydrochloride resp. alone and of its inclusion complex with beta-cyclodextrin.

The concentrations of the dissolved nicardipine and its hydrochloride resp. at room temperature were determined in clear filtrates of the saturated solutions by liquid chromatography using the external standard method.

|  | non-complexed | complexed |
| --- | --- | --- |
| nicardipine hydrochloride | 1.5 mg/ml* | 54.8 mg/ml |

-continued

| | non-complexed | complexed |
|---|---|---|
| nicardipine (base) | ** | 16.9 mg/ml |

*nicardipine hydrochloride is a crystalline substance
**nicardipine (base) is an oily substance

EXAMPLE 4

Powder X-ray diffraction

The comparison of the powder X-ray diffraction patterns of nicardipine hydrochloride (NC.HCl), beta-cyclodextrin (beta-CD), a physical mixture of nicardipine hydrochloride and beta-cyclodextrin (NC.HCl+beta-CD) and of the inclusion complex of nicardipine hydrochloride with beta-cyclodextrin (NC.HCl)-beta-CD) is shown in FIG. 1 (a, b, c, d) and in the Table. The powder X-ray diffraction pattern of the inclusion complex of nicardipine hydrochloride with beta-cyclodextrin essentially differs from that of nicardipine hydrochloride as well as from that of beta-cyclodextrin, giving proof of the individuality of the inclusion complex of nicardipine hydrochloride with beta-cyclodextrin and of the formation of a new compound, respectively. When representing powder X-ray diffraction patterns, there are often cited three spacings (d) between the lattice planes having maximum intensity (I), which for pure substances are already sufficient as a "fingerprint". These spacings are:

| NC.HCl | | beta-CD | | NC.HCl-beta-CD | |
|---|---|---|---|---|---|
| d($10^{-7}$ mm) | I | d($10^{-7}$ mm) | I | d($10^{-7}$ mm) | I |
| 3.958 | 7245 | 6.874 | 3811 | 4.878 | 1753 |
| 4.374 | 2825 | 7.009 | 2873 | 4.66 | 1637 |
| 2.835 | 1230 | 4.868 | 2587 | 4.764 | 1567 |

The resemblance between the powder pattern of beta-cyclodextrin and that of the inclusion complex of nicardipine hydrochloride with beta-cyclodextrin is in that they both show the strongest lines for the spacings between the lattice planes in the ranges from 4.5 to 5.0 and from 6.5 to 7.0. They do not, however, coincide either with respect to the spacings between the lattice planes or with respect to intensity. This resemblance can be explained by the probable resemblance of the crystalline structures of beta-cyclodextrin and of the inclusion complex of nicardipine hydrochloride with beta-cyclodextrin, which is comprehensible since the beta-cyclodextrin molecule retains the fundamental characteristics of its structure also in the complex. The powder X-ray diffraction pattern of the physical mixture of the nicardipine hydrochloride and beta-cyclodextrin shows the characteristics of both components and is completely different from that of the inclusion complex of nicardipine hydrochloride with beta-cyclodextrin.

Differential scanning calorimetry

Figure 1A:
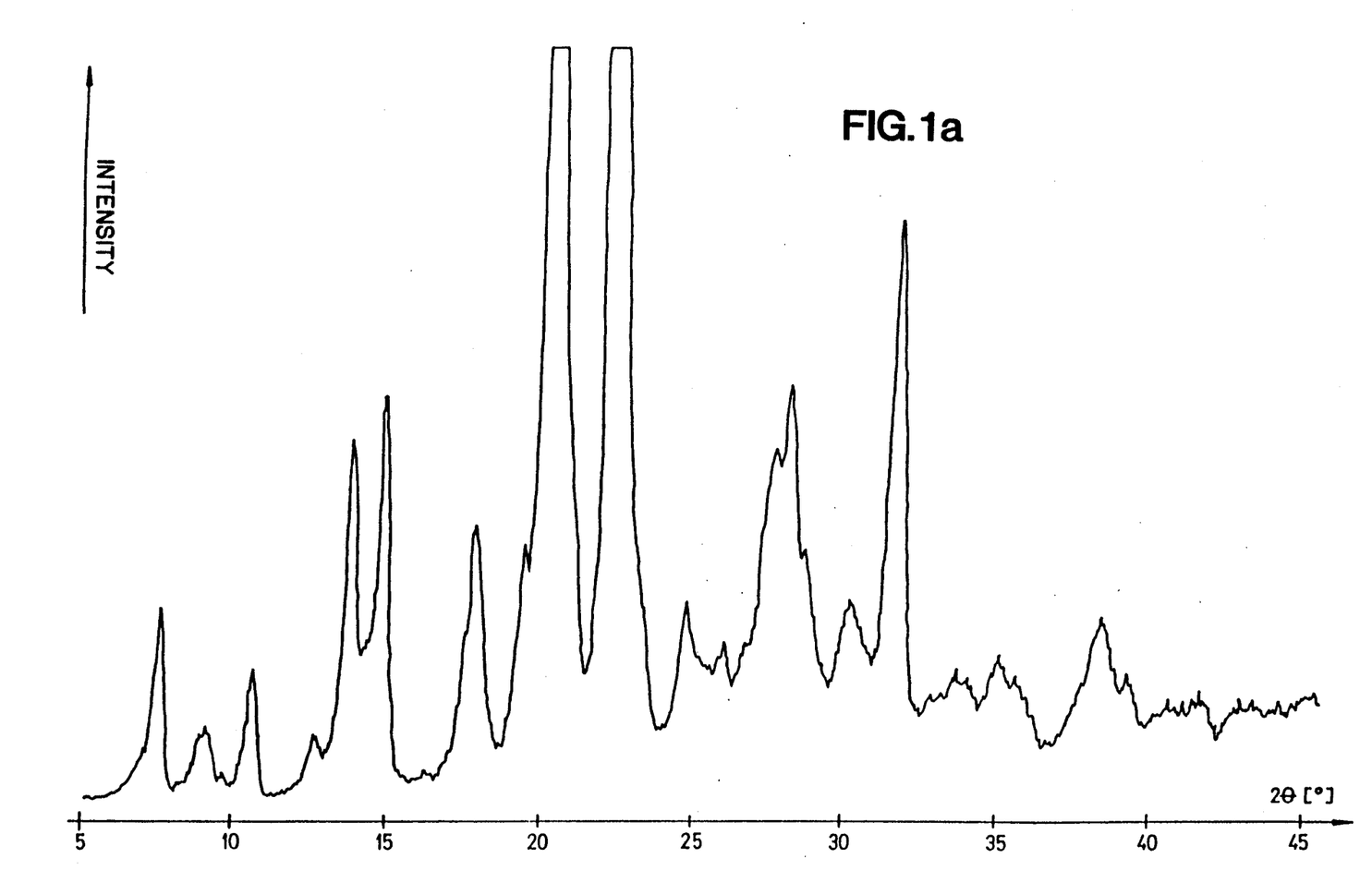
Figure 1B:
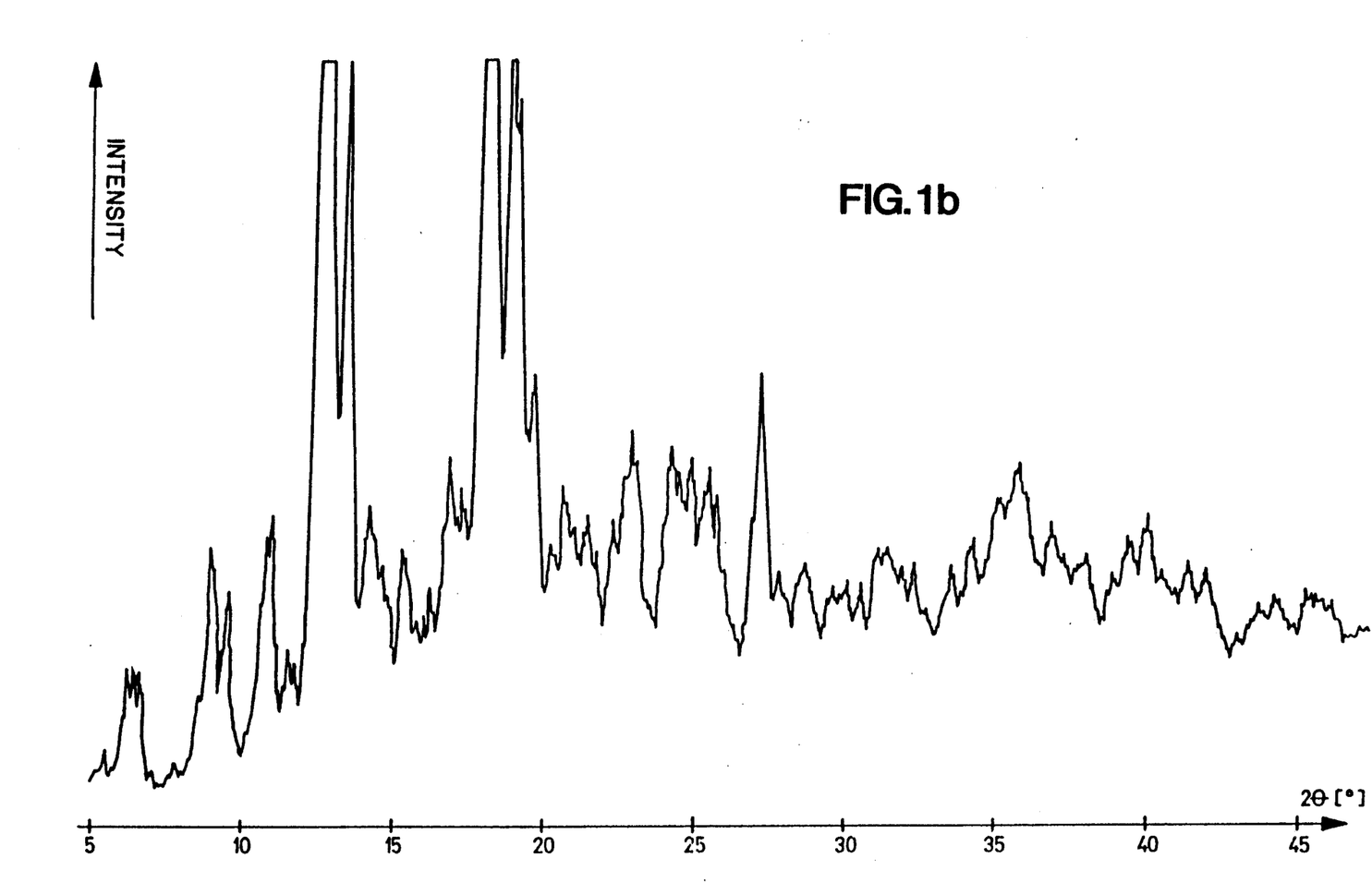
Figure 1C:
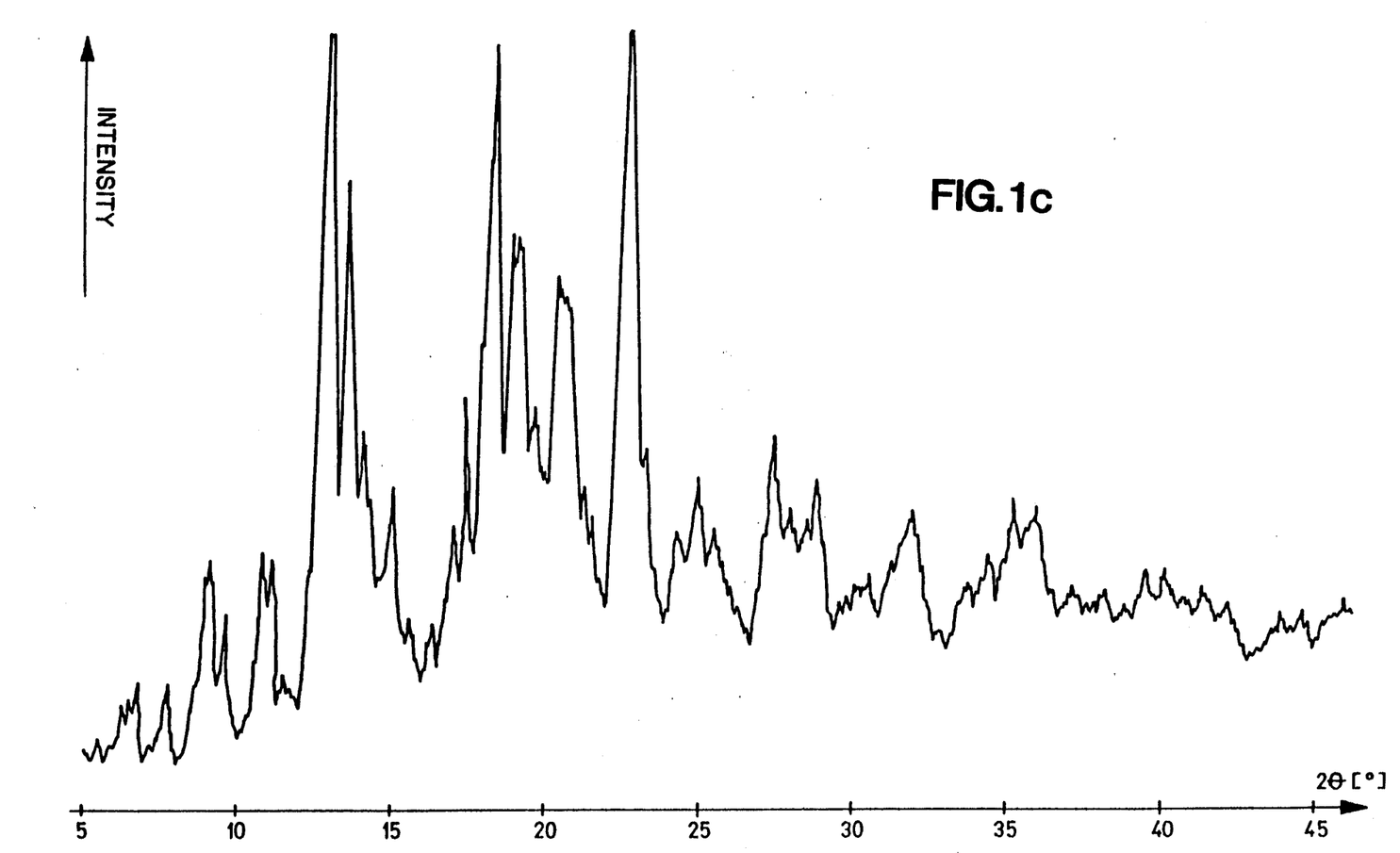
Figure 1D:
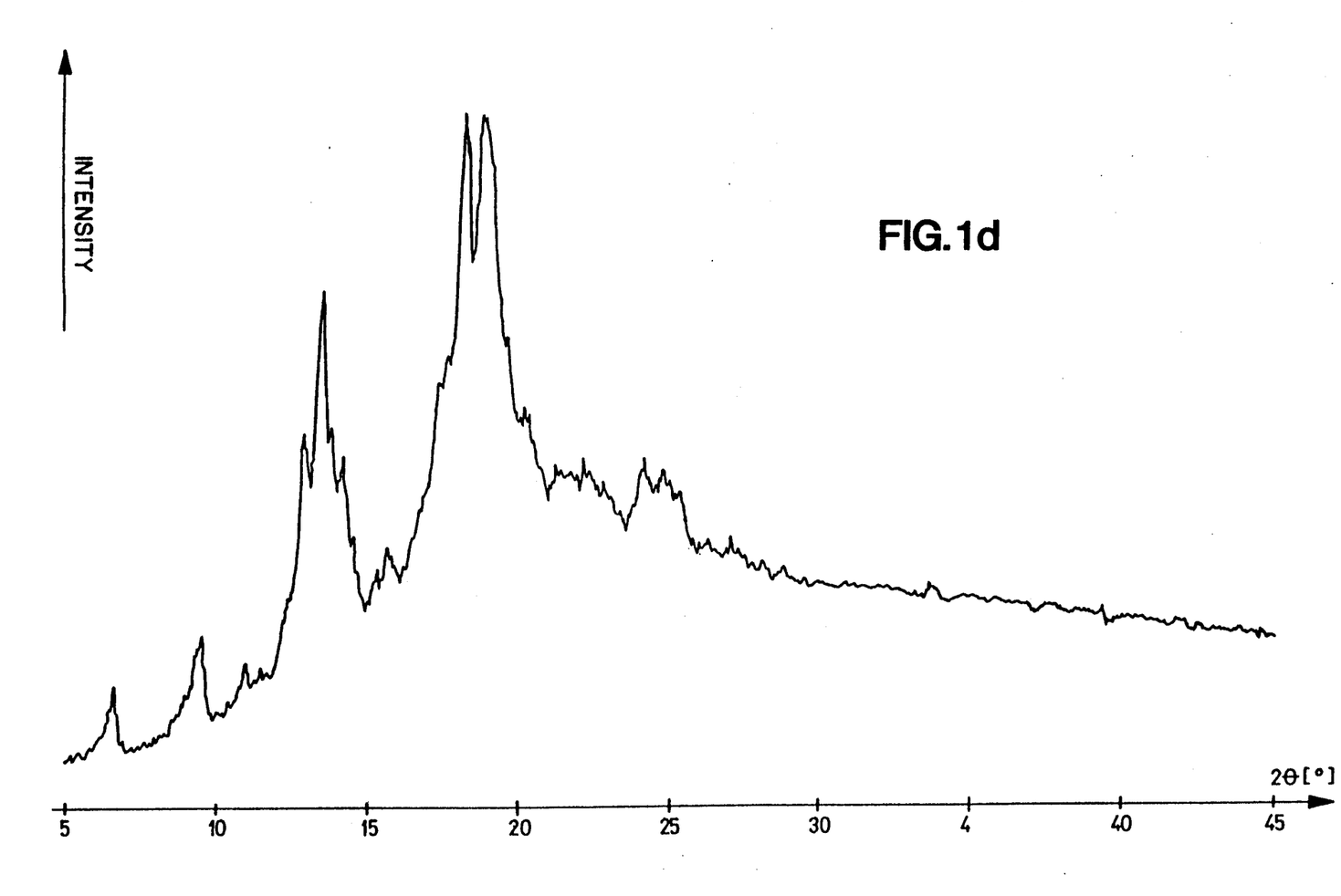
Figures 2A, 2B:
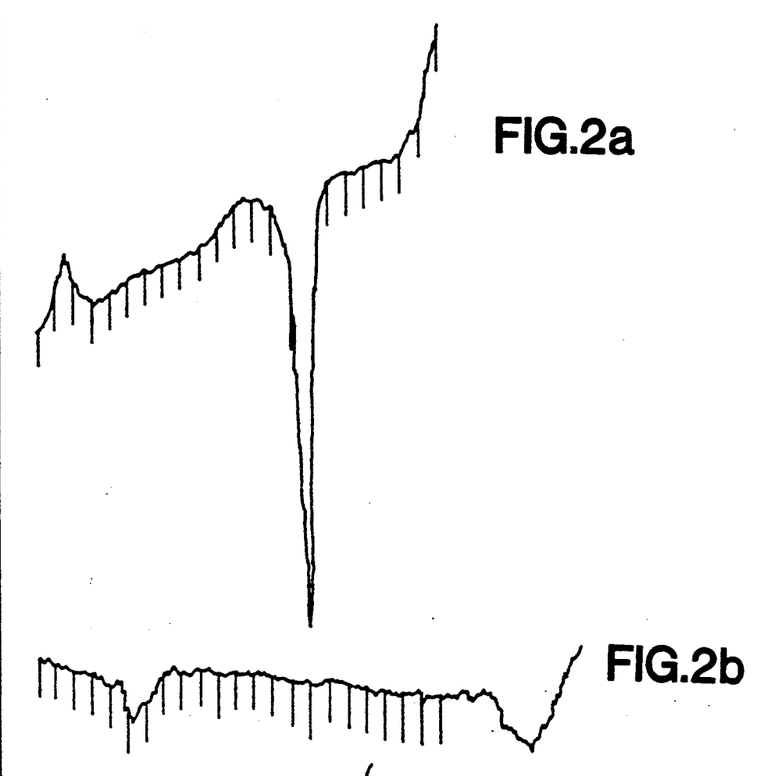
Figures 2C, 2D:
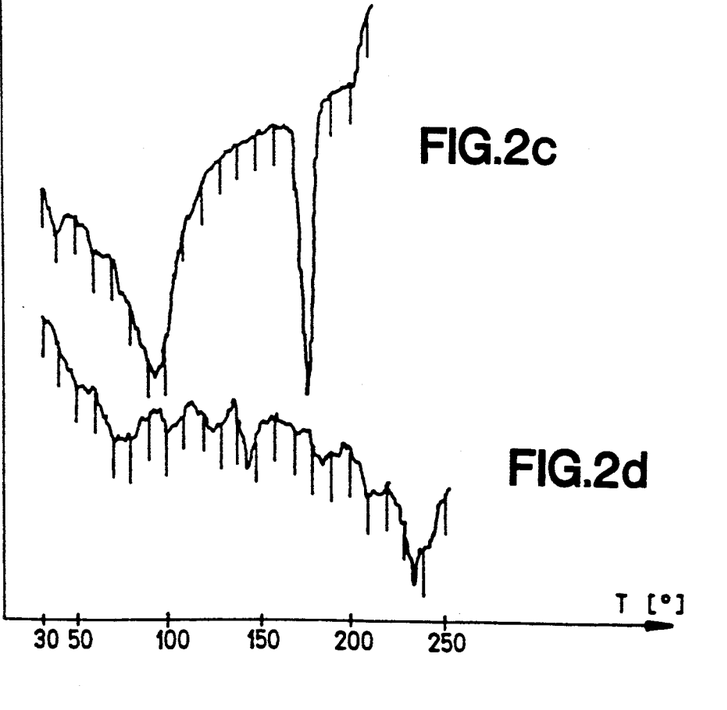

Similarly to the powder X-ray diffraction patterns the differential scanning calorimetry also shows the individuality of nicardipine hydrochloride, of beta-cyclodextrin, of a physical mixture of nicardipine hydrochloride with beta-cyclodextrin and of the inclusion complex of nicardipine hydrochloride with beta-cyclodextrin as shown in FIG. 2 (a, b, c, d). Nicardipine hydrochloride melts at 160° C., its thermal decomposition beginning at about 200° C. Beta-cyclodextrin contains combined water, which begins to separate off the sample already at about 40° C. The dehydratation of beta-cyclodextrin is completed at about 100° C. Anhydrous beta-cyclodextrin is stable up to 270° C., when thermal decomposition starts, which becomes intensive at 300° C. The behaviour of the inclusion complex of nicardipine hydrochloride with beta-cyclodextrin at the thermoanalytical assay is quite different. After the initial slight loss of weight at temperatures below 150° C., which can be attributed to the adsorbed moisture, the substance is stable up to about 220° C, when thermal decomposition sets in. The essential differences between nicardipine hydrochloride and the inclusion complex of nicardipine hydrochloride with beta-cyclodextrin lie in that the complex does not show the melting point of nicardipine hydrochloride at 160° C. and that the inclusion complex of nicardipine hydrochloride with beta-cyclodextrin is more stable as demonstrated by the onset of decomposition, which for the inclusion complex of nicardipine hydrochloride with beta-cyclodextrin is shifted for about 20° C. towards higher temperatures. The DSC scans of nicardipine hydrochloride, beta-cyclodextrin, the physical mixture of nicardipine hydrochloride and beta-cyclodextrin and of the inclusion complex of nicardipine hydrochloride with beta-cyclodextrin clearly indicate the formation of the inclusion complex of nicardipine hydrochloride with beta-cyclodextrin. Thus, the differential scanning calorimetry measurements are in accordance with the powder X-ray diffraction patterns.

EXAMPLE 5

Dissolution rates of the complexed and the non-complexed nicardipine and its hydrochloride In order to demonstrate the influence of the inclusion of nicardipine or its hydrochloride into the inclusion complex with beta-cyclodextrin upon the dissolution rate, the comparative dissolution rates of nicardipine and its hydrochloride as well as of its inclusion complex with beta-cyclodextrin in artificial biological fluids of different pH values were determined by Paddle Method on Apparatus 2 according to USP XXI (United States Pharmacopoeia Conv. 1243 to 1244 (1985)).

40 mg of nicardipine hydrochloride or the equivalent amount of 161 mg of the inclusion complex of nicardipine with beta-cyclodextrin were used.

The dissolution tests were performed in artificial gastric juice of pH 1.2 and in artificial intestinal juices of pH 6.0, 6.5 and 7.4 at the temperature of 37° C.±0.5° C. The volume of the artificial biological fluids was 1000 ml. The rotation speed of the paddle mixer was 100 rpm. The quantities of the dissolved nicardipine hydrochloride in the test samples were determined spectrophotometrically ($\lambda_{max}$=240 nm).

TABLE 1

Dissolution characteristics of the complexed and the non-complexed nicardipine and nicardipine hydrochloride in artifical biological fluids of different pH values.

| | | % dissolution(a) | | |
|---|---|---|---|---|
| | t (min.) | NC.HCl | NC.HCl-beta-CD | NC-beta-CD |
| gastric juice, pH 1.2 | 10 | 93.5 | 95.2 | 100.2 |
| | 30 | 100.2 | 100.1 | 102.0 |
| intestinal juice, pH 6.0 | 10 | 50.2 | 99.7 | 81.0 |
| | 30 | 58.7 | 100.1 | 85.3 |
| intestinal juice, pH 6.5 | 10 | 35.5 | 81.1 | 51.5 |
| | 30 | 39.0 | 85.0 | 55.9 |
| intestinal juice, pH 7.4 | 10 | 1.0 | 13.7 | 14.0 |

TABLE 1-continued

Dissolution characteristics of the complexed and the non-complexed nicardipine and nicardipine hydrochloride in artificial biological fluids of different pH values.

| | | % dissolution[a] | |
|---|---|---|---|
| t (min.) | NC.HCl | NC.HCl-beta-CD | NC-beta-CD |
| 30 | 1.3 | 15.6 | 16.4 |

Legend:
[a]The results represent the mean value of three tests.
NC.HCl = nicardipine hydrochloride
NC.HCl-beta-CD = inclusion complex of nicardipine hydrochloride with beta-cyclodextrin
NC-beta-CD = inclusion complex of nicardipine with beta-cyclodextrin From the Table 1 it is evident that in gastric juice nicardipine hydrochloride dissolves quickly and completely. A difference in the dissolution rage and extent may be observed in intestinal juice of different pH values (simulation along the intestinal tract). By the complexation of the active ingredient the dissolution rate and extent in artificial intestinal juice are essentially increased. We believe that the increase in the dissolution rate is due to the increase of the water-solubility, the decrease of the crystallinity and the increase of the wettability of the complexed nicardipine hydrochloride.

EXAMPLE 6

Acute toxicity

In toxicological tests acute toxicities ($LD_{50}$) of nicardipine hydrochloride and of its inclusion complex with beta-cyclodextrin were determined in mice and rats. The complex contained 26.8% of nicardipine hydrochloride.

Albino laboratory mice weighing 18 to 24 g and rats weighing 180 to 240 g of both sexes were used. Nicardipine hydrochloride was administered in the following doses:

mice: 1500, 3000, 4000, 5000 and 6000 mg/kg;
rats: 2000, 2500, 3000, 3500, 4000, 5000 and 6000 mg/kg.

The volume of the administered suspension was in mice 0.2 to 0.4 ml/20 g of body weight and in rats 0.8 to 2.4 ml/200 g of body weight.

The inclusion complex of nicardipine hydrochloride with beta-cyclodextrin was administered in the following doses:

mice: 18500 mg/kg of body weight, corresponding to 4958 mg of nicardipine/kg of body weight;
rats: 5000 mg/kg of body weight, corresponding to 1340 mg of nicardipine/kg of body weight,
11100 mg/kg of body weight, corresponding to 2975 mg of nicardipine/kg of body weight,
18500 mg/kg of body weight, corresponding to 4958 mg of nicardipine/kg of body weight.

The volume of the administered suspension was in mice 0.6 ml/20 g of body weight and in rats 1.2 to 4.4 ml/200 g of body weight. The animals were left without food for 18 hours before the administration. After the administration the animals were put under observation and the symptoms of poisoning or behaviour changes were recorded for another 15 days. During the tests the animals were given food and water ad libitum.

The results were statistically evaluated according to the Litchfield-Wilcoxon method (J. Pharmacol. Exp. Therap. 96, 99 (1949)).

Results

About 30 minutes after the administration of nicardipine hydrochloride, dyspnoea and paresis were observed in both animal species. The surviving animals recovered after 24 hours.

After the administration of the inclusion complex of nicardipine hydrochloride with beta-cyclodextrin, dyspnoea, paresis and tremor were observed in mice, while paresis and dyspnoea were observed in rats. The animals recovered after 24 hours.

The mortality results are shown in Tables 2, 3 and 4.

TABLE 2

Acute toxicity ($LD_{50}$) of nicardipine hydrochloride in mice after p.o. administration

| animal species | sex | dosis mg/kg body weight | No. of animals in the group | % of perished after 24 hrs | animals after 15 days | $LD_{50}$ mg/kg* after 15 days (P < 0.05%) |
|---|---|---|---|---|---|---|
| mice | M | 1500 | 10 | 0 | 0 | 3756 (2815–5012) |
| | | 3000 | 10 | 30 | 40 | |
| | | 5000 | 10 | 40 | 70 | |
| | | 6000 | 10 | 90 | 100 | |
| | F | 1500 | 10 | 20 | 20 | 3639 (2637–5022) |
| | | 3000 | 10 | 40 | 40 | |
| | | 4000 | 10 | 30 | 50 | |
| | | 5000 | 10 | 40 | 70 | |
| | | 6000 | 10 | 90 | 90 | |

*calculated according to the Litchfield-Wilcoxon method

TABLE 3

Acute toxicity ($LD_{50}$) of nicardipine hydrochloride in rats after p.o. administration

| animal species | sex | dosis mg/kg body weight | No. of animals in the group | % of perished after 24 hrs | animals after 15 days | $LD_{50}$ mg/kg* after 15 days (P < 0.05%) |
|---|---|---|---|---|---|---|
| rats | M | 2000 | 10 | 40 | 40 | 2900 (1635–5143) |
| | | 2500 | 10 | 40 | 40 | |
| | | 3500 | 10 | 60 | 60 | |
| | | 5000 | 10 | 80 | 80 | |
| | F | 3000 | 10 | 0 | 0 | 4791 (4206–5458) |
| | | 4000 | 10 | 10 | 20 | |
| | | 5000 | 9 | 44.4 | 66.6 | |
| | | 6000 | 10 | 80 | 80 | |

*calculated according to Litchfield-Wilcoxon method

TABLE 4

Acute toxicity ($LD_{50}$) of the inclusion complex of nicardipine hydrochloride with beta-cyclodextrin in mice and rats after p.o. administration

| animal species | sex | dosis mg/kg body weight | No. of animals in the group | % of perished after 24 hrs | animals after 15 days | $LD_{50}$ mg/kg* after 15 days (P < 0.05%) |
|---|---|---|---|---|---|---|
| mice | M | 18500 | 10 | 100 | 100 | <18500 |
| | F | 18500 | 10 | 100 | 100 | <18500 |
| rats | F | 5000 | 10 | 10 | 10 | >11100, |
| | | 11100 | 6 | 33.3 | 33.3 | <18500 |
| | | 18500 | 6 | 100 | 100 | |

SUMMARY

1 $LD_{50}$ of nicardipine hydrochloride in mice (M) after p.o. administration is 3756 (2815–5012) mg/kg of body weight.

2 $LD_{50}$ of nicardipine hydrochloride in mice (F) after p.o. administration is 3639 (2637–5022) mg/kg of body weight.

3 LD$_{50}$ of nicardipine hydrochloride in rats (M) after p.o. administration is 2900 (1635-5143) mg/kg of body weight.

4 LD$_{50}$ of nicardipine hydrochloride in rats (F) after p.o. administration is 4791 (4206-5458) mg/kg of body weight.

5 LD$_{50}$ of the inclusion complex of nicardipine hydrochloride with beta-cyclodextrin in mice (M and F) after p.o. administration is <18500 mg/kg of body weight (<4958 mg nicardipine hydrochloride/kg of body weight).

6 LD$_{50}$ of the inclusion complex of nicardipine hydrochloride with beta-cyclodextrine in rats (F) after p.o. administration is >1110 mg and <18500 mg (>2975 mg and <4958 mg nicardipine hydrochloride/kg of body weight).

From the obtained LD$_{50}$ values it can be concluded that there is no statistically significant difference in the toxicity of nicardipine hydrochloride and its complex with beta-cyclodextrin, respectively. From DE patent 24 07 115 it is already known that nicardipine and its hydrochloride possess a low toxicity.

EXAMPLE 7

In vitro nicardipine hydrochloride release rate from sustained release tablets

The nicardipine hydrochloride release rate from sustained release tablets was determined by the rotating basket method on Apparatus 1 according to USP XXI.

The tests were performed in artificial gastric juice, pH 1.2 (time 1.5 hours) as well as in artificial intestinal juice, pH 6.0 (up to 7 hours) at the temperature of 37° C.±5° C.

The volume of artificial biological fluids was 1000 ml. The rotation speed of the basket was 100 rpm. The times of sampling in the artificial gastric juice were 0.5, 1 and 1.5 hours after the start of the test and in the artificial intestinal juice 0.5, 1.5, 3.5 and 5.5 hours after the start of the test. A sustained release tablet was used, the composition of which is shown in Example 9 and which contains 240 mg of the inclusion complex of nicardipine hydrochloride with beta-cyclodextrin, corresponding to 60 mg of nicardipine hydrochloride.

The nicardipine hydrochloride content in the test solutions was determined quantitatively by spectrophotometric analysis, i.e. by measuring the absorption of the sample and of a standard nicardipine hydrochloride solution of known concentration at the wave length of 354 nm.

Table 5 shows the temporal course of nicardipine hydrochloride release from a sustained release tablet in artificial biological fluids at the temperature of 37° C.+0.5° C.

TABLE 5

| | t (h) | % of releae | | | | mean value |
|---|---|---|---|---|---|---|
| | | 1 | 2 | 3 | 4 | |
| artificial gastric juice, pH 1.2 | 0.5 | 9.3 | 9.1 | 9.5 | 9.7 | 9.4 |
| | 1 | 16.4 | 16.5 | 16.8 | 17.2 | 16.7 |
| | 1.5 | 21.9 | 21.8 | 22.0 | 22.6 | 22.1 |
| artificial intestinal juice, pH 6.0 | 2 | 25.8 | 25.5 | 25.9 | 25.6 | 25.6 |
| | 3 | 36.8 | 36.2 | 34.4 | 35.2 | 35.2 |
| | 5 | 66.8 | 65.8 | 66.0 | 65.6 | 65.6 |
| | 7 | 86.4 | 85.4 | 87.3 | 86.5 | 86.5 |

The results show that about 20% of nicardipine hydrochloride is released already during the stay in stomach, while the rest of the dosis is released in the intestinal juice.

EXAMPLE 8

Comparison of the bioavailabilities of nicardipine hydrochloride after p.o. administration of sustained release tablets and of the immediate release form (tablet)

Sustained release tablets containing 240 mg of the inclusion complex of nicardipine hydrochloride with beta-cyclodextrin, corresponding to 60 mg of nicardipine hydrochloride, were tested in vivo in comparison with the immediate release form (tablet) containing 20 mg of nicardipine hydrochloride. Both preparations were administered every 8 hours to 7 healthy male persons. Blood samples were taken from every person 0.5, 1. 1.5, 2, 2.5, 3, 3.5, 4, 6, 8, 12, and 24 hours after the administration of the sustained release tablets and 20 min., 40 min., 1 h, 1 h 20 min., 1 h 40 min., 2, 3, 4, 6, 8, and 12 hours after the administration of the immediate release form (tablet). Blood plasma was quickly separated and kept at −18° C. until the analysis of plasma concentrations by means of HPLC (High Performance Liquid Chromatography) method was performed.

Column: Lichrosorb Si-60, 5 μm, length 150 mm, width 4.5 mm.

Eluent: n-hexane:methanol:THF=320:20:25 (V/V/V), flow rate: 1.5 ml/min, UV detection at 350 nm.

The preparation of plasma samples:

To 3 ml of plasma there were added 50 μl of an aqueous solution of the internal standard (containing 10 mg/l of 1,4-dihydro-2,6-dimethyl-4-(3-nitrophenyl)-3,5-pyridine-(2-methoxyethyl)-dicarboxylate) and 5 ml of a 20% (V/V) solution of ethyl acetate in toluene. The resulting solution was then shaken for 1 minute, centrifugated for 5 minutes at 350 rpm, the supernatant organic phase was separated and transferred to a conical flask. The solvent was evaporated in a vacuum dryer. The walls of the flask were washed with 0.5 ml of chloroform. The solvent was again evaporated in vacuo and the walls of the flask were washed with some chloroform. The solvent was again evaporated in vacuo. The thus obtained dry extract was dissolved in 60 μl of a 1:1 (V/V) mixture of hexane:chloroform and chromatographed, using the internal standard and a calibration curve.

Figure 3:
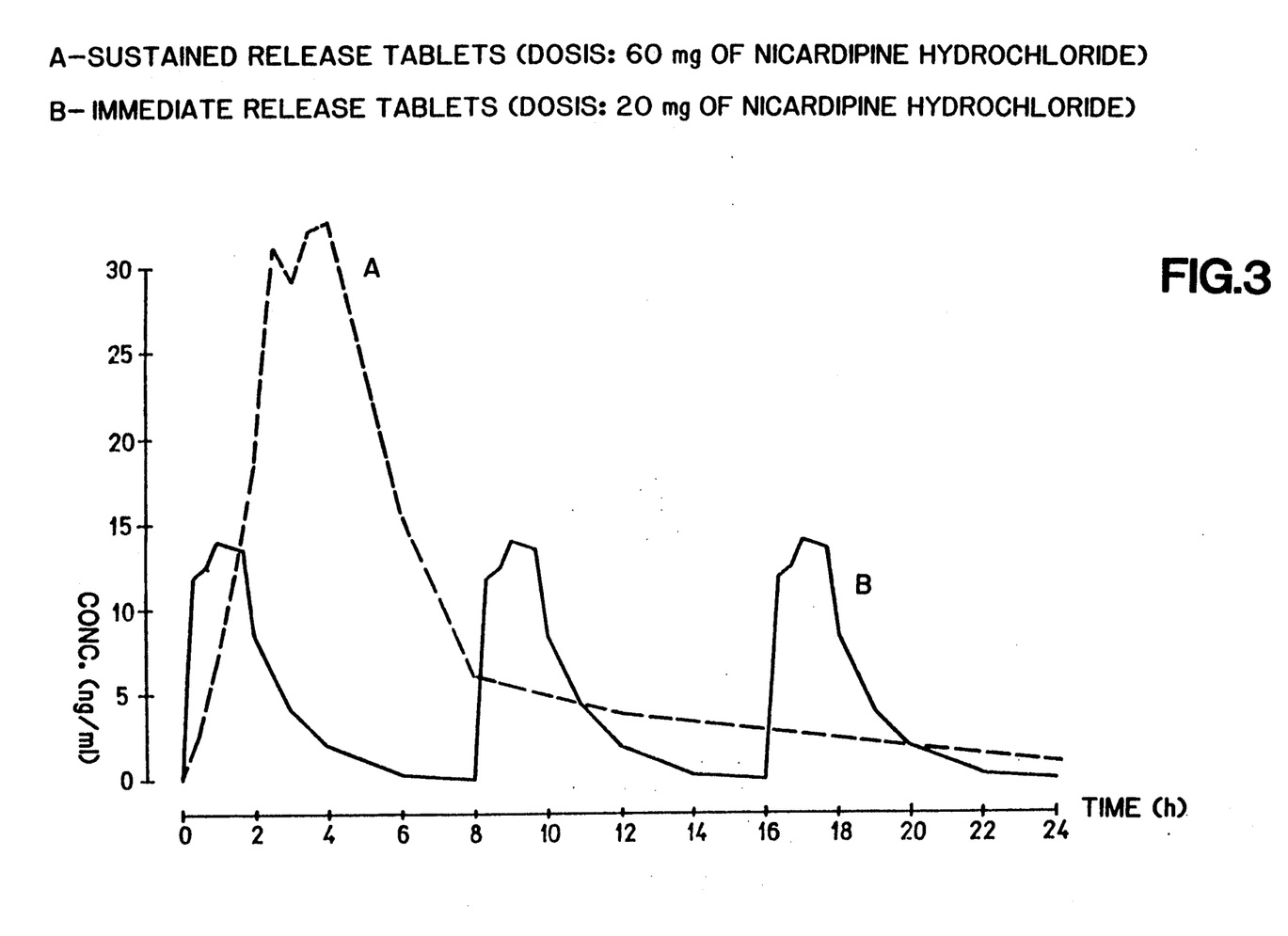

The results are shown in Table 6 and in FIG. 3.

The ingredients of the reference immediate relase tablet containing nicardipine hydrochloride are as follows:

| | |
|---|---|
| nicardipine hydrochloride | 20.0 mg |
| microcyrstalline cellulose (AVICEL PH 101) | 45.0 mg |
| lactose | 65.6 mg |
| corn starch | 11.0 mg |
| polyvinylpyrrolidone | 2.0 mg |
| talc | 4.5 mg |
| magnesium stearate | 1.2 mg |
| silica (Aerosil 200) | 0.8 mg |

TABLE 6

| | sustained release tablet 1 × 1 tablet | immediate release tablet 3 × 1 tablet (every 8 hrs) |
|---|---|---|
| AUC | 207.1 ± 79.5 (ng.h/ml) | 105.5 ± 65.8 (ng.h/ml) |
| C$_{max}$ | 42.5 ± 21.0 (ng/ml) | 22.4 ± 12.0 (ng/ml) |
| t$_{tax}$ | 3.29 ± 0.49 (h) | 0.83 ± 0.55 (h) |
| Relative bioavail- | 196.3% | 100% |

TABLE 6-continued

| | sustained release tablet 1 × 1 tablet | immediate release tablet 3 × 1 tablet (every 8 hrs) |
|---|---|---|
| ability | | |

AUC = area under the plasma concentration-time curves (mean value ± standard deviation)
$C_{max}$ = maximum plasma concentrations
$t_{max}$ = time necessary to reach the maximum plasma concentrations From Table 6 and FIG. 3 it is evident that the relative bioavailability of a sustained release tablet of nicardipine hydrochloride is almost twice as high as that of the immediate release form (tablet).

Oral sustained release pharmaceutical preparations of nicardipine hydrochloride

EXAMPLE 9

Tablets containing 60 mg of nicardipine hydrochloride in the inclusion complex with beta-cyclodextrin

| Ingredients | mg/tablet | % |
|---|---|---|
| Inclusion complex of nicardipine hydrochloride with beta-cyclodextrin (containing 25% of the active substance in the complex) | 240.0 mg | 32.2% |
| sodium alginate (Manucol ®) | 300.0 mg | 40.3% |
| microcyrstalline cellulose (AVICEL ® PH 101) | 138.5 mg | 18.7% |
| polyvinylpyrrolidone | 48.0 mg | 6.4% |
| stearic acid | 15.3 mg | 2.0% |
| magnesium stearate | 3.2 mg | 0.4% |
| | 745.0 mg | |

Procedure for the Manufacture of 10 000 tablets 2.400 kg of the inclusion complex of nicardipine hydrochloride with beta-cyclodextrin, 3.000 kg of sodium alginate and 1.385 kg of microcrystalline cellulose were passed through an oscillatory screen having a mesh size of 0.5 mm into a granulator (Loedige) and the mixture was granulated with a solution of 0.480 kg of polyvinylpyrrolidone in 1.000 kg of ethanol. The moist granulate was passed through a screen having a mesh size of 2.5 mm and the granulate was dried (Glatt WSG-15 dryer) for half an hour at an air inlet temperature of 60° to 70° C. The dry granulate was then passed through a screen having a mesh size of 0.75 mm, 0.153 kg of stearic acid and 0.032 kg of magnesium stearate were added thereto and the mix was homogeneously blended. The granulate was tableted on a rotary tablet press and there were obtained tablets having a weight of 745.0 mg and a diameter of 13 mm.

EXAMPLE 10

Tablets containing 60 mg of nicardipine hydrochloride

The procedure of Example 9 was followed, except that 0.075 kg of microcrystalline cellulose were replaced by 0.075 kg (1.0%) of glycerol ditripalmitostearate (Precirol Ato 5).

EXAMPLE 11

The procedure of Example 9 was followed, except that 0.037 kg of microcrystalline cellulose were replaced by 0.037 kg (0.5%) of sodium lauryl sulphate (Texapon K 12).

EXAMPLE 12

Capsules containing 60 mg of nicardipine hydrochloride in the inclusion complex with beta-cyclodextrin

| Ingredients | mg/capsule | % |
|---|---|---|
| Inclusion complex of nicardipine hydrochloride with beta-cyclodextrin (containing 25% of the active substance in the complex) | 240.0 mg | 38.10% |
| sodium alginate | 350.0 mg | 55.50% |
| polyvinylpyrrolidone | 37.0 mg | 5.90% |
| magnesium stearate | 3.0 mg | 0.50% |
| | 630.0 mg | |

The procedure of Example 9 was followed except that the granulate was filled into capsules.

EXAMPLE 13

Tablets containing 60 mg of nicardipine hydrochloride

| Ingredients | mg/tablet | % |
|---|---|---|
| Inclusion complex of nicardipine hydrochloride with beta-cyclodextrin | 240.0 mg | 50.0% |
| hydroxypropyl methylcellulose (Methocel ® E4M, premium) | 70.0 mg | 14.6% |
| microcyrstalline cellulose (Avicel ® PH 101) | 147.8 mg | 30.8% |
| glycerol ditripalmitostearate (Precirol Ato 5) | 15.0 mg | 3.1% |
| silica (Aerosil ® 200) | 4.8 mg | 1.0% |
| magnesium stearate | 2.4 mg | 0.5% |
| | 480.0 mg | |

Procedure for the manufacture of 20000 tablets 4.800 kg of the inclusion complex of nicardipine hydrochloride with beta-cyclodextrin, 1.400 kg of hydroxypropyl methylcellulose and 2.950 kg of microcrystalline cellulose were passed through an oscillatory screen having a mesh size of 0.5 mm into a blender (Collette type) and the mixture was blended for 10 minutes. 0.300 kg of glycerol ditripalmitostearate, 0.096 kg of silica and 0.049 kg of magnesium stearate were added and the mix was blended homogeneously. The resulting granulate was tableted on a rotary tablet press and there were obtained tablets having a weight of 480 mg and a diameter of 11 mm.

EXAMPLE 14

Capsules containing 60 mg of nicardipine hydrochloride

| Ingredients | mg/capsule | % |
|---|---|---|
| Inclusion complex of nicardipine hydrochloride with beta-cyclodextrin | 240.0 mg | 72.3% |
| hydroxypropyl methylcellulose (Methocel ® E4M, premium) | 80.0 mg | 24.1% |
| glycerol ditripalmitostearate (Precirol Ato 5) | 10.0 mg | 3.0% |
| magnesium stearate | 2.0 mg | 0.6% |
| | 332.0 mg | |

The procedure of Example 13 was followed except that the granulate was filled into capsules.

We claim:

1. The inclusion complex of nicardipine or its hydrochloride with beta-cyclodextrin.

2. The inclusion complex according to claim 1, wherein the molar ratio of nicardipine or its hydrochloride and beta-cyclodextrin is about 1:1.

3. The inclusion complex according to claim 1, wherein the molar ratio of nicardipine or its hydrochloride and beta-cyclodextrin is 1:0.0–1.1.

4. A sustained release pharmaceutical preparation for oral administration having cerebrovascular-vasodilatory and coronary-vasodilatory activity, containing as the active ingredient a therapeutically effective amount of the inclusion complex of nicardipine or its hydrochloride with beta-cyclodextrin in admixture with a pharmaceutically acceptable carrier for said inclusion complex.

5. Sustained release pharmaceutical preparations for oral administration according to claim 4, characterized in that the inclusion complex of nicardipine hydrochloride with beta-cyclodextrin contains 25 to 31% by weight of the active agent.

6. Sustained release pharmaceutical preparations for oral administration according to claim 4, characterized in that the inclusion complex of nicardipine hydrochloride with beta-cyclodextrin contains a dosage unit of 60 mg of the active agent.

7. Sustained release pharmaceutical preparations for oral administration according to claim 4 containing 30 to 80% by weight of the inclusion complex of nicardipine or its hydrochloride with beta-cyclodextrin as the therapeutically active ingredient in admixture with 40 to 56% by weight of sodium alginate or 10 to 30% by weight of hydroxypropyl methylcellulose and 1 to 5% by weight of glycerol ditripalmitostearate and from 5.0 to 6.5% by weight of polyvinylpyrrolidone or 0.1 to 3% by weight of sodium lauryl sulphate as pharmaceutically acceptable carrier for said inclusion complex.

8. Sustained release pharmaceutical preparations for oral administration according to claim 7, characterized in that the inclusion complex of nicardipine hydrochloride with beta-cyclodextrin contains a dosage unit of 40 mg of the active agent.

9. The sustained release pharmaceutical preparation of claim 7 wherein the inclusion complex of nicardipine with beta-cyclodextrin contains 14 to 18% by weight of the active agent.

* * * * *

UNITED STATES PATENT AND TRADEMARK OFFICE
CERTIFICATE OF CORRECTION

PATENT NO. : 5,079,237

DATED : January 7, 1992

INVENTOR(S) : Husu et al

It is certified that error appears in the above-identified patent and that said Letters Patent is hereby corrected as shown below:

Column 13,
In claim 3, line 3, change "1:0.0-1.1" to --1:0.9-1.1 --.

Signed and Sealed this

Fourteenth Day of September, 1993

*Attest:*

BRUCE LEHMAN

*Attesting Officer*       *Commissioner of Patents and Trademarks*